US011177042B2

(12) United States Patent
Mathis et al.

(10) Patent No.: US 11,177,042 B2
(45) Date of Patent: Nov. 16, 2021

(54) GENETIC DISEASE MODELING (71) Applicant: INTERNATIONAL BUSINESS MACHINES CORPORATION, Armonk, NY (US)

(72) Inventors: Roland Mathis, Zurich (CH); Mitra Purandare, Zurich (CH); Maria Rodriguez Martinez, Thalwil (CH)

(73) Assignee: International Business Machines Corporation, Armonk, NY (US)

( * ) Notice: Subject to any disclaimer, the term of this patent is extended or adjusted under 35 U.S.C. 154(b) by 1027 days.

(21) Appl. No.: 15/684,540

(22) Filed: Aug. 23, 2017

(65) Prior Publication Data
US 2019/0065693 A1 Feb. 28, 2019

(51) Int. Cl.
*G16H 50/50* (2018.01)
*G16B 5/10* (2019.01)
(Continued)

(52) U.S. Cl.
CPC ............ *G16H 50/50* (2018.01); *G16B 5/10* (2019.02); *G16H 20/00* (2018.01); *G16H 40/63* (2018.01)

(58) Field of Classification Search
CPC ........ G16H 50/50; G16H 20/00; G16H 40/63; G16B 5/10; G06N 5/006
See application file for complete search history.

(56) References Cited

U.S. PATENT DOCUMENTS 7,257,563 B2   8/2007  Shmulevich et al.
8,566,039 B2  10/2013  Li
(Continued)

FOREIGN PATENT DOCUMENTS

EP    2759605 A1    7/2014
WO    03065244 A9   6/2004
WO    2007067956 A3  4/2008

OTHER PUBLICATIONS

Berryhill et al., "A Complete Approach to Unreachable State Diagnosability via Property Directed Reachability," in 21st Asia and South Pacific Design Automation Conf. 127-32 (2016). (Year: 2016).*

(Continued)

*Primary Examiner* — Kamran Afshar
*Assistant Examiner* — Ryan C Vaughn
(74) *Attorney, Agent, or Firm* — Steven M. Bouknight (57) ABSTRACT

Computer-implemented methods are provided for generating a personalized Boolean model for a genetic disease of a patient. The method includes storing specification data and reference model data. The reference model includes gene nodes, representing genes, connected to Boolean circuitry and a plurality of inputs for receiving binary input values. Each gene node in the reference model comprises a multiplexer. The multiplexer has a first input and an output, a second input for receiving a binary mutation value, and a control input for receiving a binary selector value. The method further comprises using a model checker to determine if the specification is reachable in the reference model. If the specification is reachable, the method includes identifying each multiplexer whose second input was connected to its output in the path reaching the specification to obtain mutation data for the patient, generating a personalized Boolean model, and outputting personal model data.

20 Claims, 6 Drawing Sheets (51) Int. Cl.
G16H 20/00 (2018.01)
G16H 40/63 (2018.01)

(56) References Cited

U.S. PATENT DOCUMENTS

| | | |
|---|---|---|
| 8,756,080 B2 | 6/2014 | Brown |
| 2011/0202283 A1* | 8/2011 | Abdi ............... B82Y 10/00 |
| | | 702/19 |
| 2013/0116999 A1 | 5/2013 | Stein et al. |
| 2016/0283677 A1* | 9/2016 | Carmeli .............. G16H 50/20 |

OTHER PUBLICATIONS

Calzone et al., "Predicting Genetic Interactions from Boolean Models of Biological Networks," in 7 Integrative Biology 921-29 (2015). (Year: 2015).*
Dubois et al., "A Systematic Approach to the Assessment of Fuzzy Association Rules,"in 13.2 Data Mining and Knowledge Discovery 167-92 (2006). (Year: 2006).*
Silvescu et al., "Temporal Boolean Network Models of Genetic Networks and their Inference from Gene Expression Time Series," in 13 Computer Sys. 61-78 (2001). (Year: 2001).*
Arellano et al., "'Antelope': A Hybrid-Logic Model Checker for Branching-Time Boolean GRN Analysis," in 12 BMC Bioinformatics 490 (2011). (Year: 2011).*
Chockler et al., "Coverage in Interpolation-Based Model Checking," in IEEE Design Automation Conf. 182-87 (2010). (Year: 2010).*
Traynard et al., "Logical Model Specification Aided by Model-Checking Techniques: Application to the Mammalian Cell Cycle Regulation," in 32 Bioinformatics i772-i780 (2016). (Year: 2016).*
Kwon et al., "Linear Inequality LTL (iLTL): A Model Checker for Discrete Time Markov Chains," in Int'l Conf. Formal Engineering Methods 194-208 (2004). (Year: 2004).*
Akutsu et al., "Identification of Genetic Networks by Strategic Gene Disruptions and Gene Overexpressions under a Boolean Model," Theoretical Computer Science, Apr. 4, 2003, p. 235-251, vol. 298, Issue 1, Elsevier Science B.V.
Chen et al., "Boolean Models of Biological Processes Explain Cascade-Like Behavior," Scientific Reports, Jan. 29, 2016, p. 1-12, vol. 6, Article No. 20067.
Clarke et al., "Design and Synthesis of Synchronization Skeletons Using Branching Time Temporal Logic," Logic of Programs, 1981, p. 52-71, LNCS vol. 131, Springer, Berlin, Heidelberg.
Cohen et al., "Mathematical Modelling of Molecular Pathways Enabling Tumour Cell Invasion and Migration," PLOS Computational Biology, Nov. 3, 2015, p. 1-29, vol. 11, Issue 11.
Dimitrova et al., "Discretization of Time Series Data," Journal of Computational Biology, No. 6, 2010, p. 853-868, vol. 17, Mary Ann Liebert, Inc.
Fumiã et al., "Boolean Network Model for Cancer Pathways: Predicting Carcinogenesis and Targeted Therapy Outcomes," PLoS ONE, Jul. 2013, p. 1-11, vol. 8, Issue 7.
Gong et al., "Symbolic Model Checking of Signaling Pathways in Pancreatic Cancer," BICoB 2011: 3rd International Conference on Bioinformatics and Computational Biology, Mar. 23-25, 2011, 6 Pages, New Orleans, Louisiana USA.
Grieco et al., "Integrative Modelling of the Influence of MAPK Network on Cancer Cell Fate Decision," PLoS Computational Biology, Oct. 2013, p. 1-15, vol. 9, Issue 10.
Hu et al., "Integrated Network Model Provides New Insights Into Castration-Resistant Prostate Cancer," Scientific Reports, Nov. 25, 2015, p. 1-12, vol. 5, Article No. 17280.
Kauffman, "Metabolic Stability and Epigenesis in Randomly Connected Nets," Journal of Theoretical Biology, 1969, p. 437-467, vol. 22.
Konur et al., "Design and Analysis of Genetically Constructed Logic Gates," USES Conference Proceedings vol. 1, 2014, p. 31-32.
Li et al., "Comparative Study of Discretization Methods of Microarray Data for Inferring Transcriptional Regulatory Networks," BMC Bioinformatics, 2010, p. 1-6, vol. 11, No. 520, BioMed Central Ltd.
Lu et al., "Network Modelling Reveals the Mechanism Underlying Colitisassociated Colon Cancer and Identifies Novel Combinatorial Anti-Cancer Targets," Scientific Reports, Oct. 8, 2015, p. 1-15, vol. 5, Article No. 14739.
McAdams et al., "Circuit Stimulation of Genetic Networks," Science, Aug. 4, 1995, p. 650-656, vol. 269.
Melas et al., "Modeling of Signaling Pathways in Chondrocytes based on Phosphoproteomic and Cytokine Release Data," Osteoarthritis and Cartilage, 2014, p. 509-518, vol. 22, Osteoarthritis Research Society International, Elsevier Ltd.
Monteiro et al., "A Service-Oriented Architecture for Integrating the Modeling and Formal Verification of Genetic Regulatory Networks," BMC Bioinformatics, 2009, p. 1-12, vol. 10, No. 450, BioMed Central Ltd.
Queille et al., "Specification and Verification of Concurrent Systems in CESAR," International Symposium on Programming, 1982, p. 337-351, LNCS vol. 137, Springer, Berlin, Heidelberg.
Saadatpour et al., "Boolean Modeling of Biological Regulatory Networks: A Methodology Tutorial," Methods, Jul. 15, 2013, p. 3-12, vol. 62, Issue 1, Elsevier Inc.
Saez-Rodriguez et al., "A Logical Model Provides Insights into T Cell Receptor Signaling," PLoS Computational Biology, Aug. 2007, p. 1580-1590, vol. 3, Issue 8.
Shmulevich et al., "Probabilistic Boolean Networks: A Rule-Based Uncertainty Model for Gene Regulatory Networks," Bioinformatics, 2002, p. 261-274, vol. 18, No. 2, Oxford University Press.
Shmulevich et al., "From Boolean to Probabilistic Boolean Networks as Models of Genetic Regulatory Networks," Proceedings of the IEEE, Nov. 2002, p. 1778-1792, vol. 90, No. 11.
TCGA, "About TCGA," National Institutes of Health: The Cancer Genome Atlas, p. 1, https://cancergenome.nih.gov/abouttcga. Accessed on Aug. 22, 2017.
Thomas, "Boolean Formalization of Genetic Control Circuits," Journal of Theoretical Biology, Dec. 1973, p. 1-3, Elsevier Ltd., Abstract Only, http://www.sciencedirect.com/science/article/pii/0022519373902476, Accessed on Aug. 21, 2017.
Thomas, "Regulatory Networks Seen as Asynchronous Automata: A Logical Description," Journal of Theoretical Biology, 1991, p. 1-23, vol. 153, Academic Press Limited.
Thomas et al., "Dynamical Behaviour of Biological Regulatory Networks—I. Biological Role of Feedback Loops and Practical Use of the Concept of the Loop-Characteristic State," Bulletin of Mathematical Biology, Mar. 1995, p. 247-276, vol. 57, No. 2, Society for Mathematical Biology, Elsevier Science Ltd.
Thomas et al., "Multistationarity, the Basis of Cell Differentiation and Memory. I. Structural Conditions of Multistationarity and Other Nontrivial Behavior," Chaos, Mar. 2001, p. 170-179, vol. 11, No. 1, American Institute of Physics.
Xiao, "A Tutorial on Analysis and Simulation of Boolean Gene Regulatory Network Models," Current Genomics, 2009, p. 511-525, vol. 10, No. 7, Bentham Science Publishers Ltd.
International Search Report and Written Opinion of International Application No. PCT/IB2018/056076 dated Dec. 19, 2018.

* cited by examiner

| Gene Name | Driving Logic |
|---|---|
| PSA | ¬NFKB ∧ ¬CDKN2A |
| ACK1 | HSP90 |
| MAPK | ERK ∨ Androgen ∨ EGF ∨ TGFB ∨ TNFa |
| AKT | (EBP1 ∨ INPP4B ∨ Fkbp5) ∧ (HSP90 ∨ PKA_C ∨ CXCL1 ∨ TNFa ∨ PI3K) |
| AR | (FOXH1 ∨ ERBB2 ∨ EGFR ∨ FOXO1 ∨ CDKN2A ∨ DAB2IP ∨ EBP1 ∨ (SIAH2 ∧ NCor)) ∧ (AKT ∨ Androgen ∨ EP300 ∨ (Cdc37 ∧ Vav3) ∨ MED1 ∨ FHL2 ∨ CACNA1D ∨ NFKB ∨ Vav3 ∨ IL_6) |

Figure 3

| #Patient | PTEN | PSA | ACK1 | .. | MAPK | AKT | AR |
|---|---|---|---|---|---|---|---|
| 1 | .7 | .8 | .44 | .. | .5 | .6 | .7 |
| 2 | 1.5 | 1.24 | .5 | .. | .5 | 1 | .88 |
| 3 | 2.25 | 2.33 | .78 | .. | .6 | 1 | .86 |
| 4 | 1 | 1 | .67 | .. | 2 | 1.45 | 2.3 |
| 5 | 0.1 | 0.3 | .9 | .. | 3 | 4.5 | 7.8 |

| #Patient | PTEN | PSA | ACK1 | .. | MAPK | AKT | AR |
|---|---|---|---|---|---|---|---|
| 1 | 0 | 0 | 0 | .. | 0 | 0 | 0 |
| 2 | 1 | 1 | 0 | .. | 0 | 0 | 0 |
| 3 | 1 | 1 | 0 | .. | 0 | 0 | 0 |
| 4 | 1 | 1 | 0 | .. | 1 | 0 | 0 |
| 5 | 0 | 0 | 0 | .. | 1 | 1 | 1 |

Figure 7

| #Patient | Cancer State |
|---|---|
| 1 | ¬PTEN ∧ ¬PSA ∧ ¬ACK1 ∧ .. ∧ ¬MAPK ∧ ¬AKT ∧ ¬AR |
| 2 | PTEN ∧ PSA ∧ ¬ACK1 ∧ .. ∧ ¬MAPK ∧ ¬AKT ∧ ¬AR |
| 3 | PTEN ∧ PSA ∧ ¬ACK1 ∧ ..∧ ¬MAPK ∧ ¬AKT ∧ ¬AR |
| 4 | PTEN ∧ PSA ∧ ¬ACK1 ∧ .. ∧ MAPK ∧ ¬AKT ∧ ¬AR |
| 5 | ¬PTEN ∧ ¬PSA ∧ ¬ACK1 ∧ .. ∧ MAPK ∧ AKT ∧ AR |

GENETIC DISEASE MODELING

BACKGROUND

The present invention relates generally to modeling of genetic diseases, and more particularly to generation of personalized Boolean models for genetic diseases of individual patients.

Genetic diseases such as cancer can be caused by multiple mutations in complex cellular networks that cause cells to disrespect normal rules/controls of functioning/proliferation, attack normal tissues, and ultimately metastasize. Diagnosis and treatment necessitate systematic understanding of the disease, starting from molecular pathways.

Boolean models have been used for many years to model biological processes, and have been successfully applied for modelling genetic interactions to provide insights into causes and behavior of genetic diseases (see, for example: "Metabolic stability and epigenesis in randomly connected nets," Kauffman, Journal of Theoretical Biology, pp. 437-467, 1969; "A logical model provides insights into t cell receptor signaling", Saez-Rodriguez et al., PLoS Comput Biol, vol. 3, no. 8, pp. 1-11, 08 2007; and "Network modelling reveals the mechanism underlying colitis-associated colon cancer and identifies novel combinatorial anti-cancer targets," Lu et al., Scientific Reports, vol. 5, pp. 14 739 EP—, October 2015). A Boolean model integrating the main signaling pathways involved in cancer is discussed in "Boolean network model for cancer pathways: Predicting carcinogenesis and targeted therapy outcomes," Fumia and Martins, PLoS ONE, vol. 8, no. 7, pp. 1-11, 07 2013. Such Boolean models allow abstracting away precise quantitative information, representing temporal evolution of a biological process as a sequence of Boolean states.

In "Symbolic Model Checking of Signaling Pathways in Pancreatic Cancer", Gong et al, BICoB-2011, the authors apply model checking: to verify some temporal logic properties of a Boolean network modeling crosstalk of signaling pathways in pancreatic cancer. Model checkers are well-known software tools for verifying a model of a system against a specification. A model checker symbolically explores the state space of the system to check if the system has a particular behavior or, in other words, if it satisfies a particular property. A model checker automatically checks pathways through possible states of a given system model to determine if the model meets a particular specification, i.e. whether that specification is eventually reachable via a possible path through successive states of the model.

Typically, a genetic disease is not one disease but rather a collection of related diseases. Cancer, for example, is not a single disease but rather a growing collection of subtypes mapped by a large catalog of somatic mutations and characterized by tremendous molecular heterogeneity. Each patient suffering from a single type of cancer, say prostate cancer, may have different mutations and, potentially, needs a different therapy. Other multifactorial genetic diseases displaying different subtypes caused by different genetic mutations include cardiovascular disease and Alzheimer disease. A first step in diagnosis and treatment of such diseases involves obtaining gene expression data for the patient. For any patient suspected to suffer from a certain type of cancer, for example, tumor biopsy is generally performed to obtain the gene expression data. These data provide measurements such as gene transcription, methylation, phosphorylation, protein measurements, etc. for the particular disease of the patient. These data are ultimately used for diagnosis and deciding on the course of therapy.

Improved techniques for use in the diagnosis and treatment of genetic diseases would be highly desirable.

SUMMARY

According to at least one embodiment of the present invention there is provided a computer-implemented method for generating a personalized Boolean model for a genetic disease of a patient. The method includes storing specification data and reference model data. The specification data define a specification of binary measurement values obtained from gene expression data for the patient. The reference model data define a reference model modeling genetic interactions for the disease. The reference model comprises a plurality of gene nodes, representing genes, connected to Boolean circuitry and a plurality of inputs for receiving binary input values representing input stimuli for the model. Each gene node in a set of the gene nodes in the reference model comprises a multiplexer. The multiplexer has a first input and an output which connect the gene node into the model, a second input for receiving a binary mutation value, and a control input for receiving a binary selector value controlling selective connection of one of the first and second inputs to the output. In addition, any feedback loop in the model between an output of a gene node and an input thereof contains a latch. The method further comprises using a model checker to process the specification data and the reference model data to determine if the specification is reachable in the reference model via a path in which the selector value for any multiplexer in the path is selectable to permanently connect said second input to the output of that multiplexer. If the specification is thus reachable, the method includes identifying each multiplexer whose second input was connected to its output in the path reaching the specification to obtain mutation data for the patient, generating a personalized Boolean model, dependent on the mutation data and the reference model, for the patient, and outputting personal model data defining the personalized Boolean model.

Methods embodying the invention allow creation of personalized Boolean models which are differentiated according to the type of mutation that each patient exhibits. Moreover, the personalized models are generated in a highly efficient manner. Instead of introducing candidate (potential) mutations one at a time and checking after each introduction whether a patient's gene expression data are reachable via model simulation, all candidate mutations can be introduced at once through use of multiplexers with "open" selector values in a model checking operation. The open selector values are changeable and can therefore be freely selected by the model checker in analyzing the reference model, subject to a constraint explained below. This provides an elegant method for fast and efficient generation of individualized patient models. Such a model can identify and accommodate mutations underlying a particular patient's disease, facilitating individual diagnosis and targeted treatment.

The specification data may be generated automatically from the measured gene expression data for a patient. Hence, embodiments may include the steps of receiving gene expression data, comprising a plurality of non-binary measurement values, for the patient, and generating the specification data by discretizing respective non-binary measurement values to produce the binary measurement values of the specification data.

The reference model data may be generated by producing the reference model from a predefined Boolean model, e.g. a model produced by the National Cancer Institute for a particular type of cancer. Methods embodying the invention may therefore include steps of: receiving Boolean model data defining a Boolean model modeling said genetic interactions and comprising said plurality of gene nodes, said Boolean circuitry and said plurality of inputs; and generating the reference model data from the Boolean model data such that the reference model is adapted from the Boolean model by insertion in the Boolean model of each said multiplexer and each said latch. This allows predefined Boolean models from research sources to be used for generation of the reference models for model checking operations.

As discussed further below, binary mutation values for particular multiplexers, and binary input values for particular model inputs, may be specified or left open for the model checking operation as appropriate to a given case.

In general, the set of gene nodes which are represented by multiplexers in the reference model may comprise all or a subset of gene nodes in the model. Multiplexers can be used for the candidate mutations in a given case, i.e. those genes mutation of which potentially gives rise to the patient's disease. Candidate mutations might be known in some cases. In others, the set of candidate mutations is unknown. The latter case requires considering all gene nodes as potential candidates. However, particularly preferred embodiments provide a highly advantageous technique for automatically identifying potential candidates. In these embodiments, the method includes a preliminary operation for generating the reference model data. This operation includes storing preliminary model data defining a preliminary model. The preliminary model corresponds to the reference model with a multiplexer at every gene node in the model. The operation also includes generating inverse-specification data from the specification data. The inverse-specification data define an inverse-specification as the logical negation of said specification of binary measurement values. The operation further comprises using an interpolation-based model checker to process the inverse-specification data and the preliminary model data to generate a proof of reachability of the inverse-specification in the preliminary model with the first input of each multiplexer connected to the output thereof in the model. Such a proof indicates each multiplexer via which the inverse-specification is reachable. The reference model data are then generated from the preliminary model data such that the set of gene nodes which are represented by multiplexers in the reference model comprises the gene node corresponding to each said multiplexer via which the inverse-specification is reachable.

The preliminary operation thus serves to identify a set of candidate mutations for the patient, allowing restriction of the set of multiplexers in the reference model to this set of candidates. This technique can significantly reduce complexity of the main model checking operation by restricting the operation to a relevant set of candidate gene nodes. This offers exceptional efficiency, with significant savings in time and processing resources. The preliminary model data may be generated by producing the preliminary model from a predefined Boolean model as described earlier.

At least one additional embodiment of the invention provides a computer program product comprising a computer readable storage medium embodying program instructions, executable by a computing system, to cause the computing system to perform a method for generating a personalized Boolean model as described above.

At least one further embodiment of the invention provides a computing system adapted to implement a method for generating a personalized Boolean model as described above.

At least one further embodiment of the invention provides a method for obtaining a personalized Boolean model for a genetic disease of a patient. The method comprises: making gene expression measurements for the patient to obtain gene expression data comprising a plurality of non-binary measurement values; and performing a computer-implemented method described above, using said gene expression data, to obtain the personal model data defining the personalized Boolean model for the patient.

At least one further embodiment of the invention provides a method for treating a patient with a genetic disease. The method comprises: making gene expression measurements for the patient to obtain gene expression data comprising a plurality of non-binary measurement values; performing a computer-implemented method as described above, using said gene expression data, to obtain the personal model data defining the personalized Boolean model for the patient; and treating the patient in dependence on the personalized Boolean model.

Embodiments of the invention will be described in more detail below, by way of illustrative and non-limiting examples, with reference to the accompanying drawings.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g. light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments to be described may be performed as computer-implemented methods for generating personalized Boolean models for genetic diseases. The methods may be implemented by a computing system comprising one or more general—or special-purpose computers, each of which may comprise one or more (real or virtual) machines, providing functionality for implementing the operations described herein. The personalized Boolean model generation logic of the computing system may be described in the general context of computer system-executable instructions, such as program modules, executed by the computing system. Generally, program modules may include routines, programs, objects, components, logic, data structures, and so on that perform particular tasks or implement particular abstract data types. The computing system may be implemented in a distributed computing environment, such as a cloud computing environment, where tasks are performed by remote processing devices that are linked through a communications network. In a distributed computing environment, program modules may be located in both local and remote computer system storage media including memory storage devices.

Figure 1:
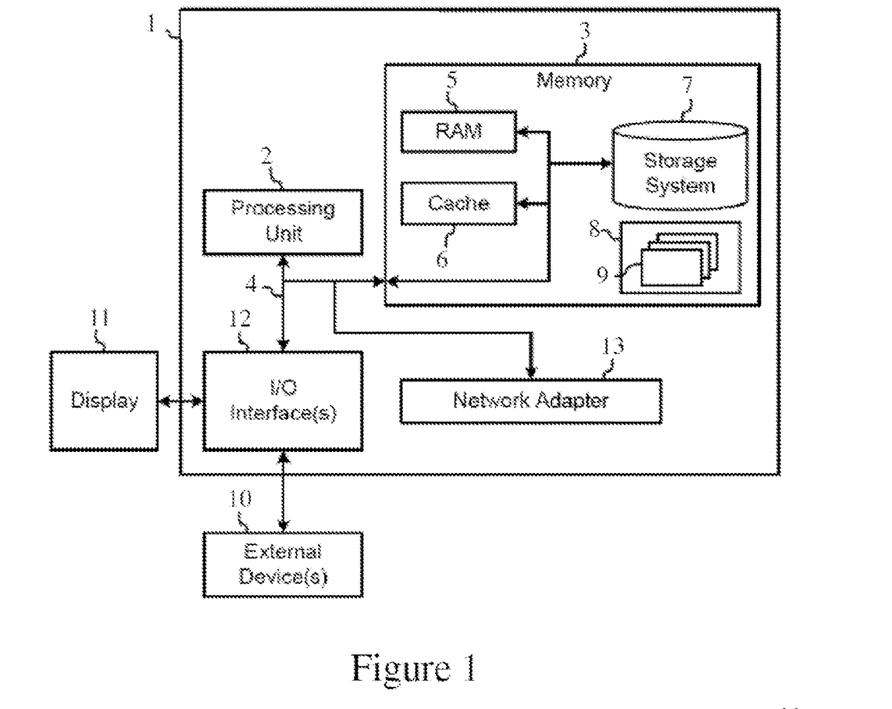
FIG. 1 is a schematic representation of a computer for implementing personalized Boolean model generation methods embodying the invention.

FIG. 1 is a block diagram of exemplary computing apparatus for implementing personalized Boolean model generation methods embodying the invention. The computing apparatus is shown in the form of a general-purpose computer 1. The components of computer 1 may include processing apparatus such as one or more processors represented by processing unit 2, a system memory 3, and a bus 4 that couples various system components including system memory 3 to processing unit 2.

Bus 4 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer 1 typically includes a variety of computer readable media. Such media may be any available media that is accessible by computer 1 including volatile and non-volatile media, and removable and non-removable media. For example, system memory 3 can include computer readable media in the form of volatile memory, such as random access memory (RAM) 5 and/or cache memory 6. Computer 1 may further include other removable/non-removable, volatile/non-volatile computer system storage media. By way of example only, storage system 7 can be provided for reading from and writing to a non-removable, non-volatile magnetic medium (commonly called a "hard drive"). Although not shown, a magnetic disk drive for reading from and writing to a removable, non-volatile magnetic disk (e.g. a "floppy disk"), and an optical disk drive for reading from or writing to a removable, non-volatile optical disk such as a CD-ROM, DVD-ROM or other optical media can also be provided. In such instances, each can be connected to bus 4 by one or more data media interfaces.

Memory 3 may include at least one program product having one or more program modules that are configured to carry out functions of embodiments of the invention. By way of example, program/utility 8, having a set (at least one) of program modules 9, may be stored in memory 3, as well as an operating system, one or more application programs, other program modules, and program data. Each of the operating system, one or more application programs, other program modules, and program data, or some combination thereof, may include an implementation of a networking environment. Program modules 9 generally carry out the functions and/or methodologies of embodiments of the invention as described herein.

Computer 1 may also communicate with: one or more external devices 10 such as a keyboard, a pointing device, a display 11, etc.; one or more devices that enable a user to interact with computer 1; and/or any devices (e.g. network card, modem, etc.) that enable computer 1 to communicate with one or more other computing devices. Such communication can occur via Input/Output (I/O) interfaces 12. Also, computer 1 can communicate with one or more networks such as a local area network (LAN), a general wide area network (WAN), and/or a public network (e.g. the Internet) via network adapter 13. As depicted, network adapter 13 communicates with the other components of computer 1 via bus 4. It should be understood that although not shown, other hardware and/or software components could be used in conjunction with computer 1. Examples include, but are not limited to: microcode, device drivers, redundant processing units, external disk drive arrays, RAID systems, tape drives, and data archival storage systems, etc.

A first method embodying the invention is described below with reference to FIGS. 2 to 11. This method uses gene expression data for a patient, and a predefined Boolean model for the type of genetic disease exhibited by the patient. Such Boolean models integrating key signaling pathways involved in a disease may be obtained from a variety of research sources. The present embodiment is described for a patient suffering from cancer, and uses examples of data provided by The Cancer Genome Atlas (TCGA). TCGA was launched by the National Cancer Institute (NCI) and the National Human Genome Research Institute (NHGRI) in 2006 as a pilot project to comprehensively characterize the genomic and molecular features of ovarian cancer and glioblastoma multiforme. The program grew to include samples from 11,000 patients across 33 tumor types and represents the largest tumor collection ever to be analyzed for key genomic and molecular characteristics. Findings for 13 cancer types have already been published, and by late 2014, TCGA scientists had nearly completed sequencing protein-coding regions (exomes) for most tumor types, and completed whole-genome sequencing (WGS) for 1,000 tumor samples. The latter characterizes the complete DNA sequence in the genome. Results from TCGA analyses to date have led to more than 2,700 articles in research journals. Examples used herein are in whole or part based upon data generated by the TCGA Research Network.

Figure 2:
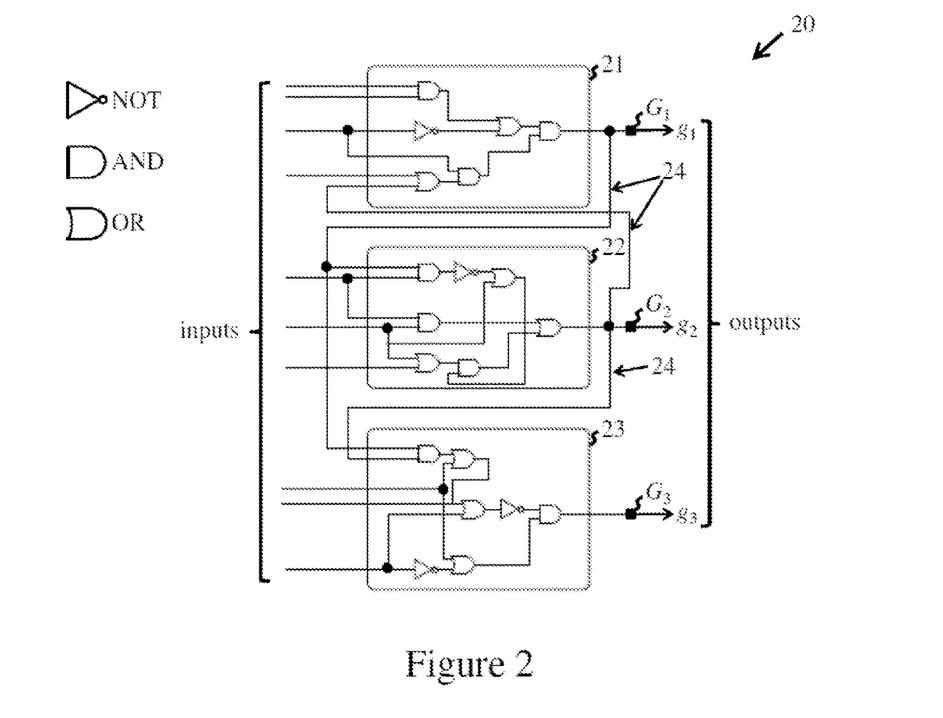
FIG. 2 shows an example of a Boolean model.

FIG. 2 shows a simple example 20 of a Boolean model modelling genetic interactions. The Boolean model is a directed graph with two types of nodes: a gene node (which represents a particular gene) and a gate node. A gate node can be a logical AND gate node, an OR gate node, or NOT gate node. A node evaluates to either '0' or '1'. A node can be driven by either a gene or a gate. In the example shown, nodes G1, G2 and G3 are gene nodes. The gene nodes are connected to Boolean circuitry comprising the gate nodes. All gate nodes driving the individual gene nodes are shown encapsulated in square boxes 21, 22 and 23 in the figure. The model has a plurality of inputs for receiving binary input values representing input stimuli for the model, i.e. input signals which drive the logic expressed by the model. The particular inputs are defined for the model in question. The gene nodes provide the outputs of the model. In particular, the output signals are the binary gene node values, denoted by g1, g2 and g3 in the figure. The model includes a number of feedback connections between an output of a gene node G1, G2 or G3 and an input thereof. The feedback connections are indicated at 24 in the figure. The outputs g1, g2 and g3 of the model will therefore be updated as feedback values and/or input values vary in the model.

Figure 3:
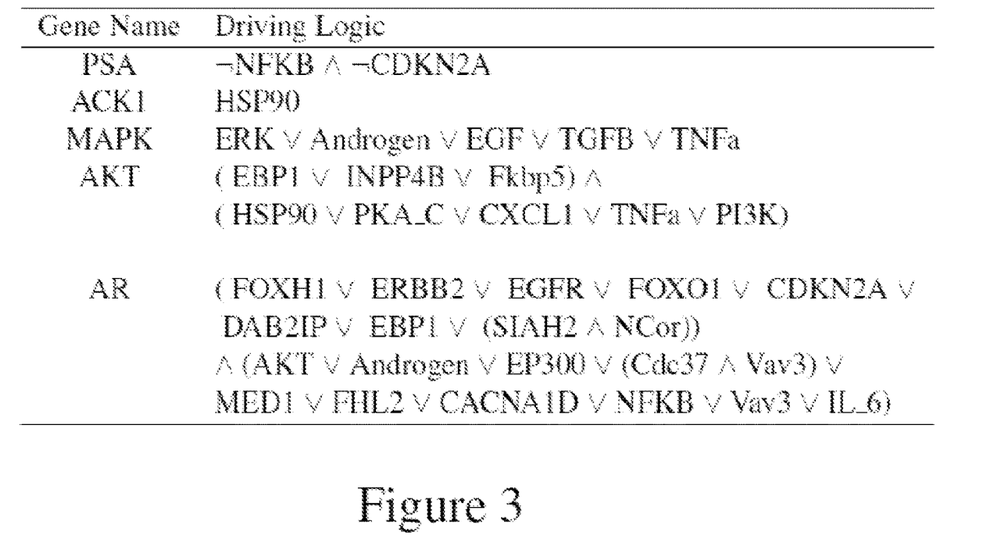
FIG. 3 illustrates description of a Boolean model in terms of logical Boolean formulae.

A Boolean model can also be represented in terms of Boolean formulae defining the logic driving each output node. FIG. 3 provides an illustrative example of a model described as logical Boolean formulae. In this example, gene names corresponding to output gene nodes are shown in the left-hand column. The right-hand column indicates the driving logic for each gene node in terms of the logical operators ¬ (NOT), ∧ (AND), ∨ (OR) and names of gene nodes/input stimuli driving that node. Updating a gene node in this context simply involves evaluating the Boolean formula driving the gene node. The update scheme here can be synchronous (all gene nodes are updated at the same time) or asynchronous (only one randomly selected gene node gets updated at any time).

The input stimuli for a given Boolean model will depend on the particular nature and extent of the model. Input stimuli may, for example, represent environmental and/or biological factors (e.g. environmental/biological triggers or other indicators/related factors such as carcinogens, growth factors, properties associated with androgens, proteins, methylation, phosphorylation, etc.,) relevant to a disease. Binary input values may represent presence or absence of the associated stimuli and/or high or low states for the stimuli, e.g. high or low concentrations, values, etc. Input stimuli may also represent outputs of external nodes (e.g. gene nodes of another interrelated model such as a larger model of which the current model forms a part). In particular, a Boolean model may be a part of a larger, more complex model expressing more extensive interactions for the disease. Inputs to such a model may therefore correspond to connections (e.g. gene node outputs) from another composite part of the larger model. In general, inputs may represent any quantities relevant to the particular disease and model in question, and it suffices to understand that the particular inputs are defined as appropriate for the model in question.

While FIG. 1 shows a simple model, Boolean models representing genetic diseases can be more complex models involving many more gene nodes (e.g. hundreds of gene nodes), and might include nodes corresponding to other quantities (e.g. proteins, methylation or phosphorylation values, etc.,) where the interactions between such quantities have been appropriately modeled. However, operation of methods embodying the invention can be fully understood from the principles description herein and illustrated below with reference to the model of FIG. 1.

Figure 4:
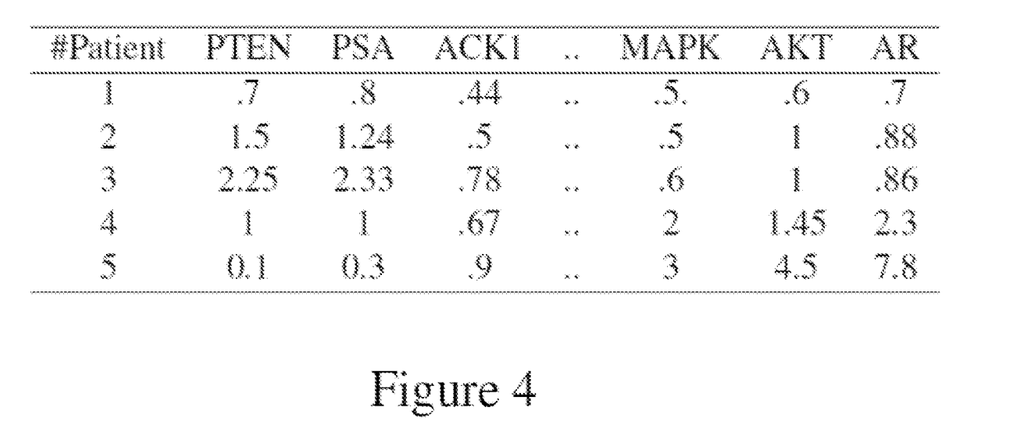
FIG. 4 shows an example of gene expression data for patients.

FIG. 4 illustrates an example of gene expression (also referred to as "transcription") measurements for a series of patients. Patients are identified by numbers in the left-hand column. The remaining columns indicate the gene expression measurements corresponding to respective genes identified by name, e.g. PTEN, PSA, ACK1, in the column headers. Each row of the table provides gene expression data, comprising a series of (non-binary) measurement values, for a particular patient. While gene values are shown in the example here, in general gene expression data may include other measurement values, e.g. measurements relating to proteins, methylation, phosphorylation, etc., as relevant to a patient's disease.

Figure 5:
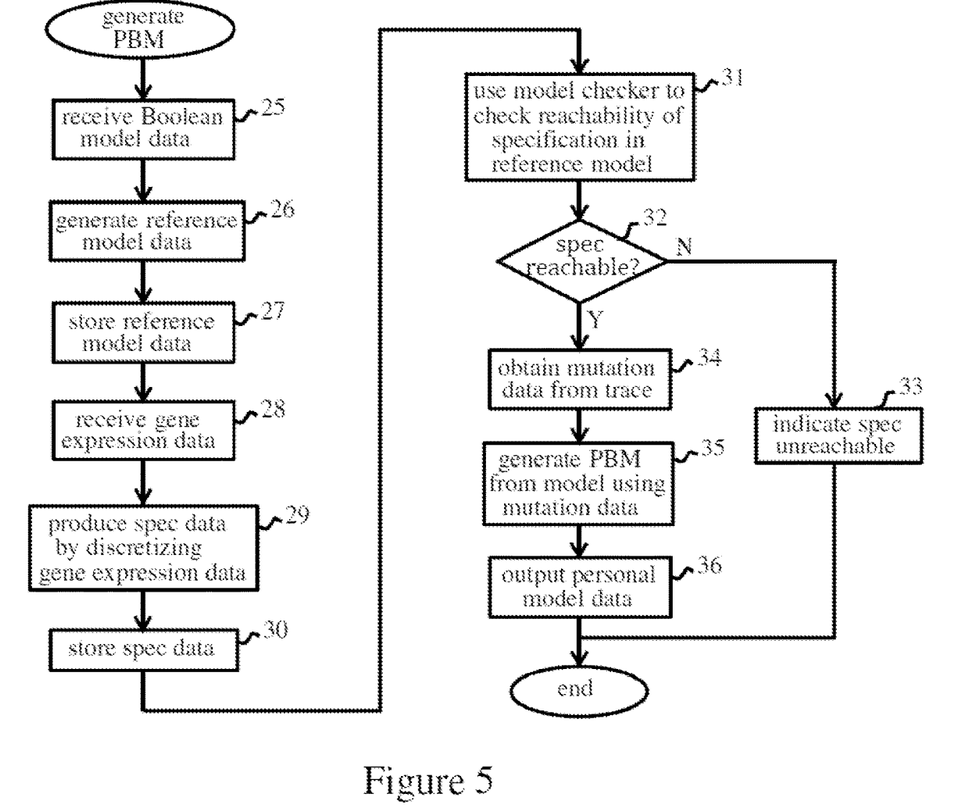
FIG. 5 indicates steps of a first model generation method embodying the invention.

The flow diagram of FIG. 5 indicates steps of the first method for generating a personalized Boolean model. This method is based on a predefined "healthy" Boolean network model integrating the main signaling pathways involved in a patient's cancer type, and gene expression data for the patient. (Note that, in general, steps of flow diagrams may be performed in a different order to that shown, and some steps may be performed concurrently as appropriate). Step 25 represents receipt by the computing system of data defining the predefined Boolean model. In step 26, the computing system uses this Boolean model data to generate reference model data. The reference model data define a reference model for the subsequent operation. This reference model is adapted from the Boolean model by insertion in the Boolean model of a set of multiplexers, and one or more latches as required. In particular, in this embodiment each gene node in the reference model comprises a multiplexer. Each multiplexer has a first input and an output which connect the gene node into the model, a second input for receiving a binary mutation value, and a control input for receiving a binary selector value controlling selective connection of one of the first and second inputs to the output of the multiplexer. In addition, any feedback loop in the model between an output of a gene node and an input thereof contains a latch. The reference model generation operation will be discussed further below. In step 27, the resulting reference model data are stored in memory of the computing system.

Step 28 represents receipt by the computing system of the gene expression data for the patient. As described earlier, these data comprise a series of non-binary measurement values. In step 29, the computing system generates specification (spec) data, defining a specification of binary measurement values, using the gene expression data input in step 28. These specification data are generated as detailed further below by discretizing respective non-binary measurement values in the gene expression data to produce corresponding binary measurement values. In step 30, the resulting specification data are stored in memory of the computing system.

In step 31, the computing system uses a model checker to process the specification data and the reference model data to determine if the specification of binary measurement values for the patient is reachable in the reference model via a path in which the selector value for any multiplexer in the path is selectable to permanently connect its second input to its output. Hence, the selector values for the multiplexers are left open, i.e. can be freely chosen by the model checker, subject to the constraint that once a selector value is set to connect the second input, and hence a binary mutation value, to a multiplexer output, it must remain that way permanently in the path reaching the specification (and the mutation value itself will remain unchanged). The specification thus defines a statement of requirements, or "reachability property" for the model checker. The model checker determines if this specification can be satisfied by the reference model, i.e. whether there is a possible path through states of the reference model via which that specification can be reached, subject to the aforementioned constraint on selector values in the path. Particular input values for the reference model, and binary mutation values for particular multiplexers, may be left open or may be specified the model checking operation as discussed further below.

Allowing for the possibility that the specification is not reachable (as indicated by a "No" (N) at decision block 32), this will be indicated by the model checker. Operation would then proceed to step 33 in which the computing system here would simply indicate this fact to an operator, e.g. by displaying a message. Such an event would be unlikely for any accurate model, and would require reassessment of system parameters, e.g. modification of any constraints on input values or binary mutation values, reassessment of discretization thresholds (discussed below), possible adjustment of the model, etc. However, any such actions are orthogonal to the main operation described herein which assumes, as will generally be the case, that the specification is reachable. This fact will again be indicated by the model checker resulting in a positive decision ("Yes" (Y)) at decision 32. In particular, the model checker will provide an output, or "trace", indicating the path via which the specification was reached. As explained further below, this trace will thus indicate the chosen selector values for multiplexers in the path reaching the specification. In step 34, the computing system identifies from the trace each multiplexer whose second input was connected to its output in the path reaching the specification to obtain mutation data for the patient. In step 35, the computing system then generates a personalized Boolean model, dependent on the mutation data and the reference model, for the patient. Steps 34 and 35 are explained in more detail below. In step 36, the computing system outputs personal model data defining the personalized Boolean model, and operation is complete.

Figure 6:
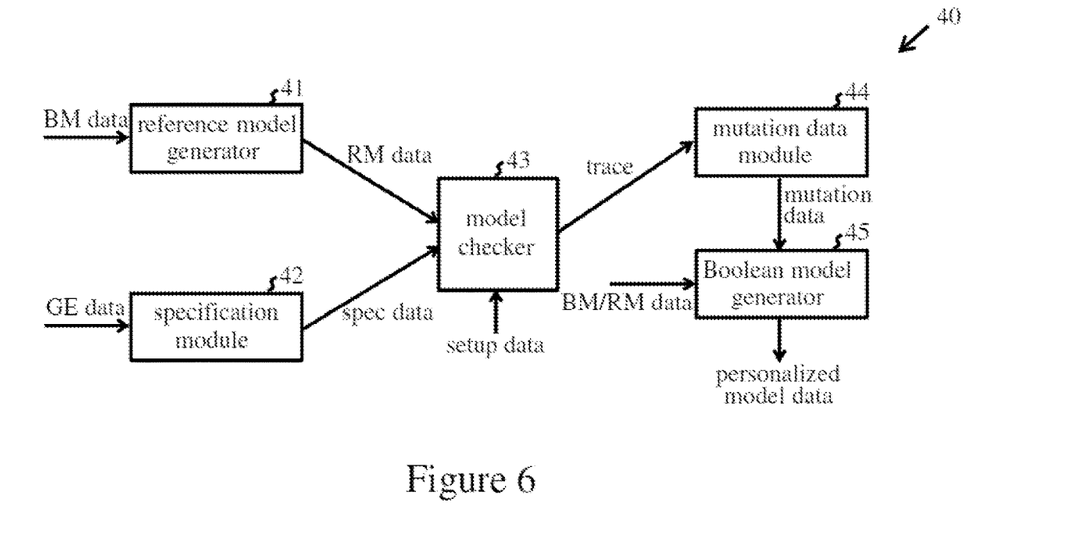
FIG. 6 is a schematic illustration of component modules of a computing system implementing the FIG. 5 method.

FIG. 6 is a schematic representation of logic comprising component modules, e.g. program modules, in an exemplary computing system for performing the FIG. 5 method. The system 40 includes a reference model generator module 41 which receives the Boolean model data (BM data) input in step 25, and generates the reference model data (RM data) in step 26. A specification module 42 receives the gene expression data (GE data) input in step 28 and performs step 29 to generate the specification data. System 40 includes an in-built model checker tool 43 in this embodiment. The model checker 43 receives the reference model data and specification data from modules 41 and 42 respectively, and performs the model checking operation described above. Setup data may be provided to the model checker to specify any additional operating parameters, e.g. operating constraints and/or defined input/mutation values as discussed below. Such setup data may alternatively be included in the reference model data. A mutation data module 44 receives the output trace from model checker 43 and performs step 34 to generate the mutation data. These data are supplied to a Boolean model generator 45 which performs steps 35 and 36, generating the personalized Boolean model. The personalized model is dependent (directly or indirectly) on the reference model used by the model checker 43. In particular, the personalized model may be generated from the reference model per se, based on the reference model data from module 41, or from the original Boolean model from which the reference model was derived, based on the Boolean model data received in step 25. The Boolean model generator 45 then outputs the personal model data defining the personalized Boolean model.

Note that functionality of one or more modules in FIG. 6 may be combined. For example, a model generator module may combine functions of modules 41 and 45. Functionality may also be differently distributed between component modules of a computing system, and functionality of one or more modules may be implemented independently of the computing system. The specification data, for example, may be independently generated, e.g. by an operator, and supplied as input to the computing system. Reference model generator 41 may also be independently implemented, whereby FIG. 5's operation would commence with input and storage of reference model data in step 27. A reference model generated for one patient may also be applicable to another, whereby a library of previously-generated reference models may be stored for use by the computing system.

Also, while system 40 implements the model-checking operation here using a local model checker, e.g. a plug-in model checker tool, embodiments can be envisaged in which the computing system uses a remote model checker, e.g. provided as a service in the cloud, to perform the model checking operation.

Figure 7:
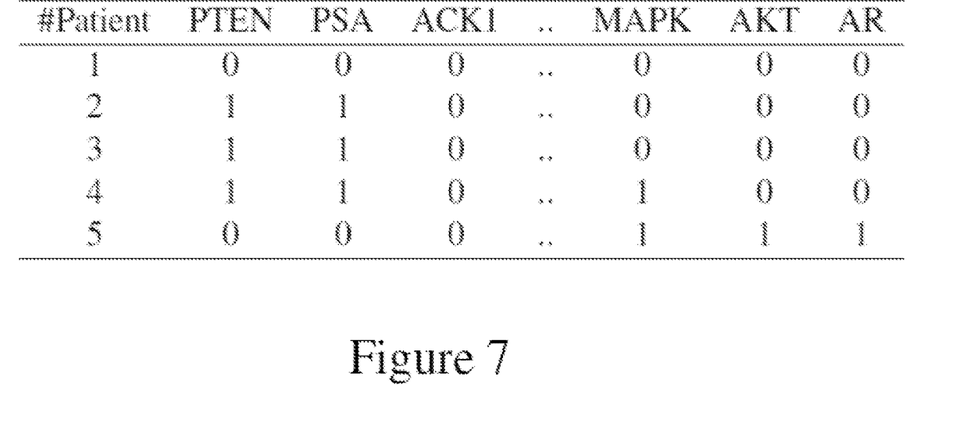
FIG. 7 indicates discretized gene expression measurement values corresponding to the data of FIG. 4.

Operation of the modules of system 40 will now be explained in more detail. Specification module 42 generates the specification data from the gene expression data by discretizing non-binary measurement values in the gene expression data, and formulating the specification as a logical formula which defines the reachability property for the model checker. Discretization of gene expression measurement values requires conversion of the values to binary. FIG. 7 provides a simple illustration of discretization for the FIG. 4 data. Here, a measurement value v in FIG. 4 is converted to a binary value b in FIG. 7 using a predefined threshold for the gene in question. For PTEN, for instance, b=1 if v≥1, and b=0 otherwise. A value b=0 in FIG. 7 indicates that the gene is turned OFF. A value b=1 indicates that the gene is turned ON. Hence, Patient #1 has all genes turned off. Patient #2 has PTEN and PSA turned ON and ACK1, ..., MAPK, AKT, AR turned OFF. The threshold for discretizing different types of measurement value may be different and may be selected as appropriate for a given type, e.g. based on usual ranges and distributions of the values. Various techniques, such as clustering, are known for discretizing analog data, and any desired technique may be used here. Particular examples are described in: "Comparative study of discretization methods of microarray data for inferring transcriptional regulatory networks", Li et al, BMC Bioinformatics, vol. 11, p. 520, 2010; and "Discretization of time series data", Dimitrova et al., Journal of Computational Biology, vol. 17, no. 6, pp. 853-868, 2010.

Figure 8:
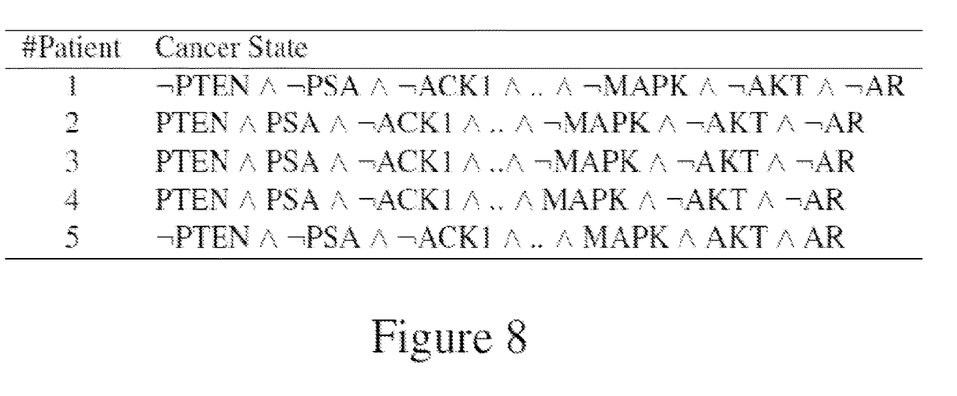
FIG. 8 indicates model-checking specifications corresponding to the discretized measurement values of FIG. 7.

The discretized gene expression values are characteristic to each patient and represent his/her disease state. After discretizing the gene expression values, specification module 42 produces a logical formula defining the specification. FIG. 8 illustrates how each row in FIG. 7 can be converted to a Boolean formula using logical operators ¬(NOT) and ∧(AND). Each gene is a variable in the formula. If a gene G has a value '0', it appears as a negative literal (¬G) in the formula. If a gene has a value '1', it appears as a positive literal (G) in the formula. The final formula is a conjunction of all the gene literals and describes the patient's cancer state. The specification data define the specification as a reachability property for the model checker, here by prefixing it with the CTL (Computation Tree Logic) operator EF. A reachability property EF(G1∧G2) states that there exists a path for a model which eventually reaches a state satisfying G1=1 and G2=1.

Figure 9:
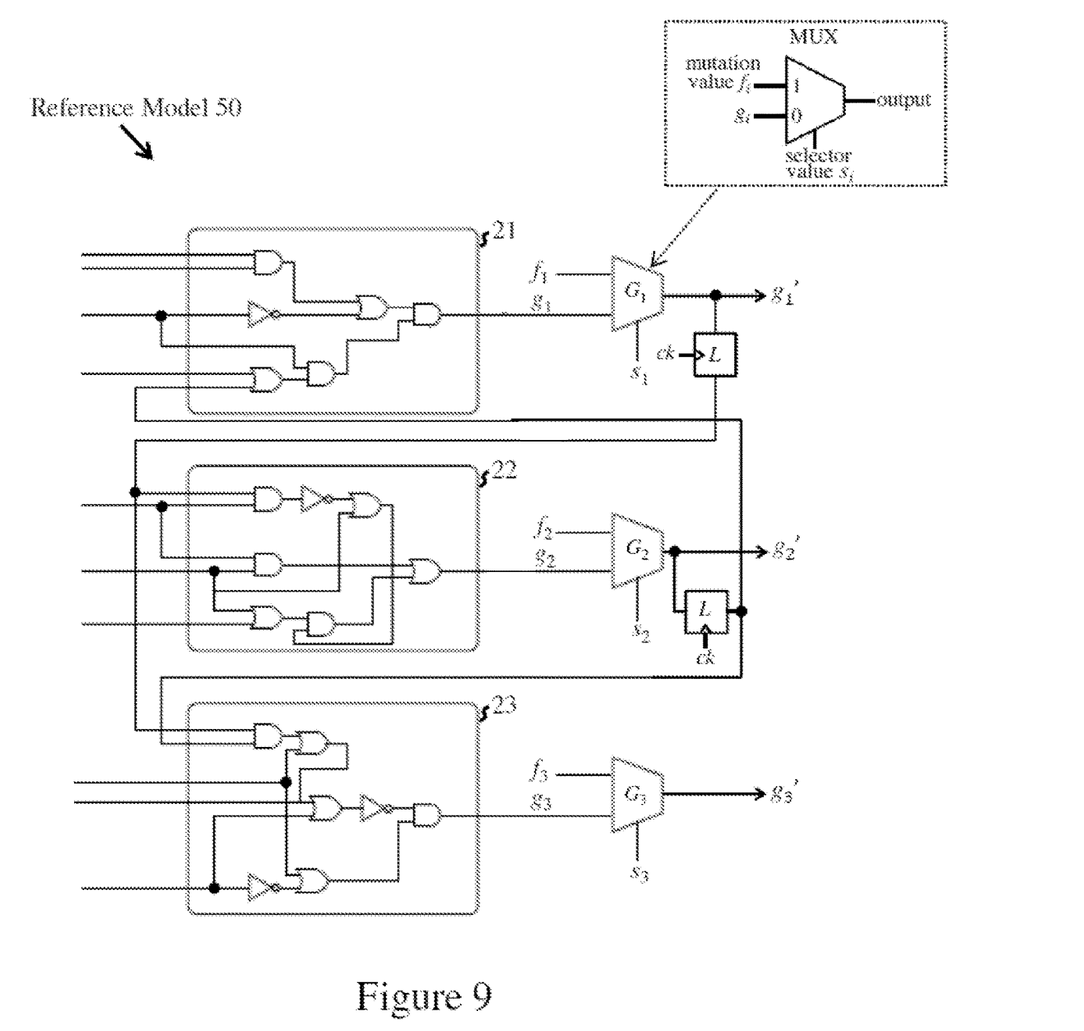
FIG. 9 illustrates a reference model corresponding to the Boolean model of FIG. 2.

Reference model generator module 41 generates the reference model from the input Boolean model here by converting the Boolean model to an HDL (Hardware Description Language) model in which multiplexers and latches are inserted as described above. FIG. 9 shows an example of a reference model 50 produced from the Boolean model of FIG. 2. In this embodiment, a multiplexer (MUX) is inserted for each gene node G1, G2 and G3. As indicated in the enlargement, each multiplexer has a first input (#0) and an output which connect the gene node into the model, and a second input (#1). The first input #0 thus receives the original gene expression value $g_i$ for a gene node $G_i$. The second input #1 receives a binary mutation value $f_i$. Each multiplexer also has a control input for receiving a binary selector value $s_i$ which controls selective connection of one of the two inputs to the output. In addition, a latch L is inserted in any feedback loop in the model between an output of a gene node and an input of a gene node. Hence a latch L is inserted in feedback paths 24 of the FIG. 2 model as indicated in FIG. 9. The latches are clocked by a clock signal ck and thus break the loops in the original Boolean model, allowing clocking of the model through a succession of states. The gene outputs in each state are denoted by gi' in the figure.

When a selector value si is set to '0' in the reference model, first input #0 is connected to the multiplexer output. Otherwise, the second input #1 is connected to the output. For a gene Gi, if si is '0', the unmutated gene value gi is connected to the multiplexer's output and the remaining nodes see Gi as unmutated (gi'=gi). If si is '1', the mutation value fi appears at the output and the rest of the nodes see Gi as mutated (gi'=fi). In general, there are two kinds of mutations: a gene turned ON or a gene turned OFF forever. These two mutations correspond to fi=1 and fi=0, respectively. If the nature of any particular gene mutation (i.e. gene on/off) is known, the mutation value fi may be predefined in the reference model. Otherwise, the mutation value fi can be left open.

A model in which the genes reach expression values described in the specification data for a patient is said to be personalized for that patient. Hence, a personalized model for a patient, when simulated, must reach a state described by the discretized gene expression values in the specification. Let us call this a discrete cancer state φ. A straightforward way to check whether a model reaches this state would be to: 1. introduce a candidate mutation; 2. simulate the model to check if the cancer state is reachable; 3. if so output the model; 4. if not, repeat steps 1 to 3 for the next mutation. Here, the steps must be repeated for all candidate mutations, and the approach is incomplete in that one does not know if all states have been checked. In contrast, the use of multiplexers in the reference model as described above allows all mutations to be introduced at once, allowing the model checker to check all possible states.

Model checker 43 operates in generally known manner to determine whether the specification, defined by reachability property EFφ, is reachable in the reference model subject to the constraint on selector values si described above. In particular, the selectors of the multiplexers are kept open (not driven to either '0' or '1') so that model checker 43 is free to select the values of si. As the selector values are open, they assume random values which can change multiple times on a path which is un-intended. Reset logic is applied to set the initial selector values for a starting state of the model. When a reset is active, the selector values are set to '1' or '0' at random. However, once a mutation is activated, it must remain active throughout the path. Hence, once a given selector value si is set to '1' in model checker 43, it must remain at '1' permanently for the path. With this constraint, model checker 43 thus checks possible paths through states of the reference model to determine if the reachability property EFφ characteristic to the patient is eventually reachable. Mutation values fi may be left open for selection by the model checker where not specified for a gene node, and may be randomly assigned during reset. Once a particular mutation value fi is selected, the value remains the same throughout the path. The binary input value for a reference model input may be specified in the reference model data if the particular input value is known (e.g. presence or absence of a health factor). Otherwise the input value can be left open.

Figure 10:
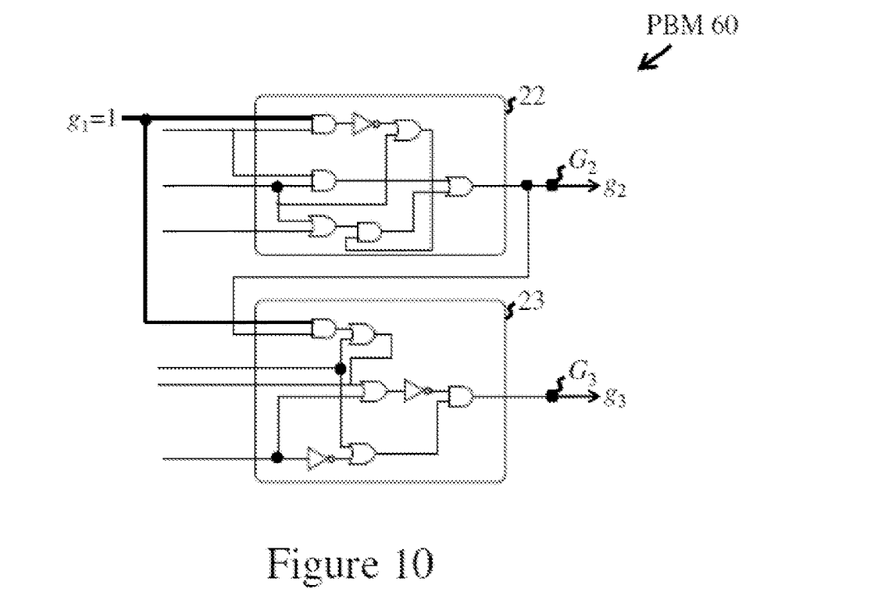
FIG. 10 shows an example of a personalized Boolean model obtained using the reference model of FIG. 9.

If there is a combination of mutations that makes EFφ reachable, model checker 43 returns a trace reaching EFφ. Such traces are of generally known form and indicate values (including values selected by the model checker) for the variables defined in successive states of a model in the path via which the specification was reached. This trace will thus indicate the chosen selector values for multiplexers in the path reaching the specification. The selector variables si with value '1' on this trace show which mutations are triggered, and thus identify the particular mutations that resulted in the patient's cancer state φ. Mutation data module 44 identifies gene nodes with si=1 in the trace. Where the corresponding mutation value fi was left open, the value of fi selected in the path to φ is also extracted from the trace, together with any input values which were left open for the reference model and thus selected by the model checker. The resulting data constitute the mutation data output by module 44 and used by model generator 45 to generate the personalized model for the patient. Model generator 45 can generate the personalized Boolean model by adapting the original predefined, healthy model input in step 25 of FIG. 5 according to the mutation data. Any gene node Gi for which a mutation was triggered to value fi can be replaced in the original model by that value, and the corresponding driving logic can be removed from the model. FIG. 10 illustrates this process with an example. Here, a personalized Boolean model (PBM) 60 is generated from the FIG. 2 model for the case where mutation of gene Gi to value fi=1 (i.e. Gi switched ON) was indicated in the trace. This process can be used to adapt the original Boolean model for all mutations triggered in reaching the patient's cancer state. The personal model data defining the resulting personalized model are then output by model generator 45. The output data may define the personalized model in any convenient manner here, e.g. as a diagrammatic representation such as FIG. 10 or as Boolean formula, as desired.

It can be seen that the above method provides a systematic and efficient technique for formal computation of a personalized disease model given a reference Boolean model of pathways involved in a particular type of disease and a set of candidate mutations. All candidate mutations are introduced in the healthy Boolean model in such a way that a model checker can be exploited to identify mutations that lead to the cancer state.

Figure 11:
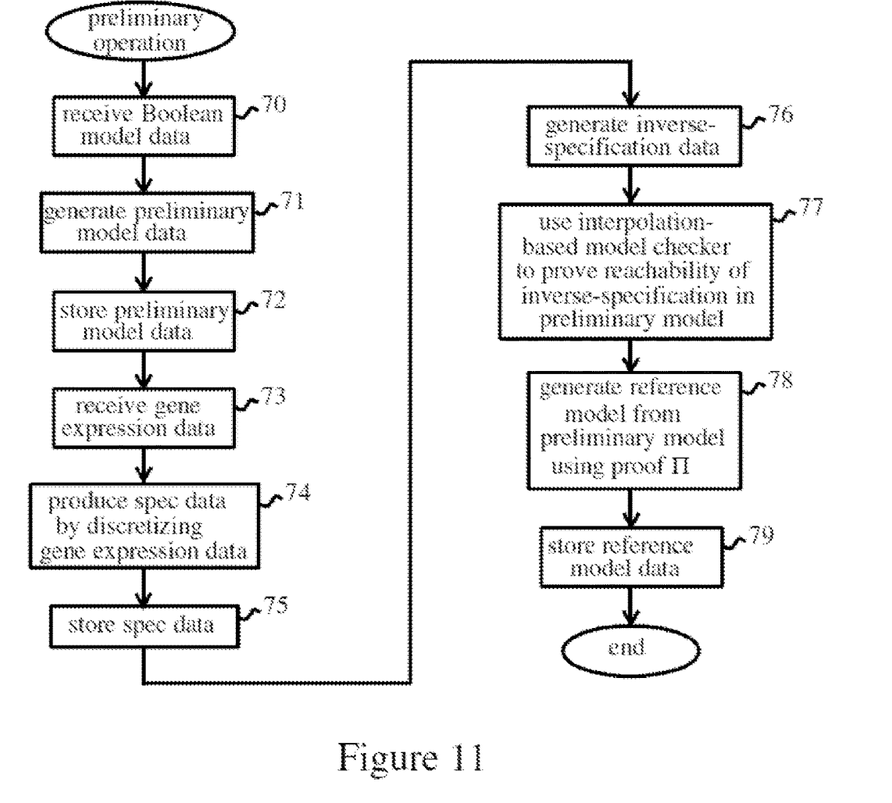
FIG. 11 indicates steps of a second model generation method embodying the invention.

In a modification to the above embodiment, the set of gene nodes represented by multiplexers in the reference model may be a subset of gene nodes in the model corresponding to a known set of candidate mutations for the patient. A second method embodying the invention provides a highly-efficient technique for identifying relevant candidate mutations to be included in this set. This embodiment includes a preliminary operation for identifying relevant candidates and generating the reference model data accordingly. FIG. 11 indicates steps of the preliminary operation. Step 70 corresponds to step 25 of FIG. 5 in which data defining the predefined Boolean model are received by the computing system. In step 71, the computing system generates preliminary model data defining a preliminary model. This preliminary model corresponds to the reference model as described for FIG. 5 with a multiplexer at every gene node in the model. Preliminary model data defining this preliminary model are stored in step 72. Steps 73 to 75 correspond to steps 28 to 30 respectively of FIG. 5. In step 76, the system generates inverse-specification data defining an inverse-specification as the logical negation of the specification of binary measurement values in the specification data stored in step 75. For a specification φ, the inverse-specification is defined as ¬φ. The inverse-specification thus corresponds to the negation of the reachability property, e.g. $\neg EF(G1 \wedge G2)$ for a reachability property $EF(G1 \wedge G2)$.

In step 77, the computing system uses an interpolation-based model checker to process the inverse-specification data and the preliminary model data to generate a proof of reachability of the inverse-specification in the preliminary model with the first input of each multiplexer connected to the output thereof in the model. The selector values for all multiplexers are thus set to si=0 for the model checking operation. In this configuration, the reference model corresponds to the original healthy Boolean model. We call this configuration of the model RM0. The patient's cancer state $\phi$ is unreachable in RM0 since a normal/healthy Boolean model does not reach a cancer state. However, by construction, we know that RM0 $\vDash \neg \phi$, i.e. the inverse specification is certainly reachable in RM0. In step 77, the model checker will therefore generate a resolution proof Π for $\neg \phi$ on RM0. Such resolution proofs produced by interpolation-based model checkers are of generally known form, and indicate a series of resolution steps via which the required state (here $\neg \phi$) is proven to be reachable. The proof Π will thus indicate each multiplexer via which the inverse-specification $\neg \phi$) is reachable by specifying the corresponding selector variables si=0 in the proof. All the selector variables si (and hence multiplexers) absent from the proof do not contribute to the satisfaction of $\neg \phi$) by RM0. Hence, the corresponding genes Gi, when mutated, do not result in $\phi$ being satisfied in the mutated model and should be ignored.

In step 78, the system then generates the reference model data from the preliminary model data such that the set of gene nodes which are represented by multiplexers in the reference model comprises the gene nodes identified as relevant by the proof, i.e. the gene nodes corresponding to those multiplexers via which the inverse-specification $\neg \phi$ is reachable in RM0. The other multiplexers, corresponding to the "non-candidate" genes, are discarded from the model. This can be achieved by removing these multiplexers from the preliminary model, or simply by tying all selector values for these multiplexers to si=0 in the reference model. The reference model data are then stored in step 79.

Following the preliminary operation, subsequent operation of this embodiment corresponds to steps 31 to 36 of FIG. 5, whereby the main model-checking operation of step 31 is restricted to the relevant set of candidate mutations. This offers exceptional efficiency in the personalized model generation process.

Modules 41 to 45 of the FIG. 6 system can be adapted to implement the additional functionality required for the preliminary operation above, or additional modules may be provided for these functions. The interpolation-based model checking operation of step 77 may thus be performed by model checker 43 which performs the main model checking operation of step 31. Alternative embodiments may use different model checkers for the two operations if desired.

Personalized Boolean models generated via the foregoing methods can be used in systematic diagnosis and therapy specific to each patient, and can further help in identifying effective treatment(s) to cure the disease. By providing a formal symbolic analysis which is complete and more efficient than step-by-step simulations, methods embodying the invention may help in identifying/classifying genetic mutations and matching them with medications or other potential treatments. Models may also assist efforts aimed simulating the whole disease network and predicting optimal medications based on the global cellular response to medication perturbations.

Methods embodying the invention may be integrated in processes for diagnosis and treatment of patients by medical personnel. Such processes may include making gene expression measurements for a patient to obtain gene expression data, and performing a computer-implemented method as described above, using the gene expression data, to obtain a personalized Boolean model for the patient. The process may then include treating the patient in dependence on the personalized Boolean model. For example, identification of specific mutations/mutation sets may be used to select appropriate medication(s) targeting specific causes, effects or contributory factors for an individual's disease, or otherwise to decide on particular therapies or treatment combinations for a personalized treatment plan.

Various changes and modifications can of course be made to the exemplary embodiments described. For example, the personalized model generation process may be performed in a composite manner based on a number of interconnected, component models making up a larger more complex model. The final personalized model may then be constructed from the collated results for the individual components.

Methods embodying the invention may of course be applied to genetic diseases other than cancer, and measurement values used in the specification data may include any additional values accommodated by the model in question.

In general, where features are described herein with reference to a method embodying the invention, corresponding features may be provided in a computing system embodying the invention, and vice versa.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for generating a personalized Boolean model for a genetic disease of a patient, the method comprising:
   storing preliminary model data defining a preliminary model, the preliminary model corresponding to a reference model with a multiplexer at every gene node in the reference model;
   generating inverse-specification data from specification data, the inverse-specification data defining an inverse-specification as the logical negation of a specification of binary measurement values;
   using an interpolation-based model checker to process the inverse-specification data and the preliminary model data to generate a proof of reachability of said inverse-specification in the preliminary model with a first input of each multiplexer connected to an output thereof, said proof indicating each said multiplexer via which the inverse-specification is reachable; and
   generating said reference model data from the preliminary model data such that a set of gene nodes in the reference model comprises a gene node corresponding to each said multiplexer via which the inverse-specification is reachable;

storing the specification data defining the specification of binary measurement values obtained from gene expression data for the patient;

storing reference model data defining the reference model modeling genetic interactions for the disease, the reference model comprising a plurality of gene nodes, representing genes, connected to Boolean circuitry and a plurality of inputs for receiving binary input values representing input stimuli for the model, wherein each gene node in the set of said gene nodes comprises the multiplexer having the first input and the output which connect the gene node into the model, a second input for receiving a binary mutation value, and a control input for receiving a binary selector value controlling selective connection of one of the first and second inputs to said output, and wherein any feedback loop in the model between an output of a gene node and an input thereof contains a latch;

using a model checker to process the specification data and the reference model data to determine if said specification is reachable in the reference model via a path in which the selector value for any multiplexer in the path is selectable to permanently connect said second input to the output of that multiplexer;

if said specification is reachable, identifying each multiplexer whose second input was connected to its output in the path reaching the specification to obtain mutation data for the patient, and generating a personalized Boolean model, dependent on said mutation data and the reference model, for the patient; and outputting personal model data defining said personalized Boolean model.

2. The method of claim 1, further comprising:
receiving gene expression data, comprising a plurality of non-binary measurement values, for the patient; and
generating said specification data by discretizing respective non-binary measurement values to produce said binary measurement values.

3. The method of claim 1, further comprising:
receiving Boolean model data defining a Boolean model modeling said genetic interactions and comprising said plurality of gene nodes, said Boolean circuitry and said plurality of inputs; and
generating said reference model data from the Boolean model data such that said reference model is adapted from said Boolean model by insertion in the Boolean model of each said multiplexer and each said latch.

4. The method of claim 1, further comprising: for each of one or more of said multiplexers, specifying said binary mutation value for use by the model checker for that multiplexer.

5. The method of claim 1, further comprising: for each of one or more of said multiplexers, defining said binary mutation value for that multiplexer to be selectable by the model checker.

6. The method of claim 5, wherein said mutation data indicates the binary mutation value selected by the model checker for each said multiplexer whose second input was connected to its output in reaching the specification.

7. The method of claim 1, further comprising:
receiving Boolean model data defining a Boolean model modeling said genetic interactions and comprising said plurality of gene nodes, said Boolean circuitry and said plurality of inputs; and
generating said preliminary model data from the Boolean model data such that said preliminary model is adapted from said Boolean model by insertion in the Boolean model of each said multiplexer and each said latch.

8. The method of claim 1, further comprising:
receiving gene expression data, comprising a plurality of non-binary measurement values, for the patient;
generating said specification data by discretizing respective non-binary measurement values to produce said binary measurement values; and
for each of one or more of said multiplexers, defining said binary mutation value for that multiplexer to be selectable by the model checker.

9. The method of claim 1, further comprising: specifying one or more of said binary input values for use by the model checker.

10. The method of claim 1, further comprising: defining one or more of said binary input values to be selectable by the model checker.

11. The method of claim 2, further comprising:
making gene expression measurements for the patient to obtain gene expression data comprising a plurality of non-binary measurement values; and
using said gene expression data to obtain said personal model data defining the personalized Boolean model for the patient.

12. The method of claim 2, further comprising:
making gene expression measurements for the patient to obtain gene expression data comprising a plurality of non-binary measurement values;
using said gene expression data to obtain said personal model data defining the personalized Boolean model for the patient; and
treating the patient in dependence on the personalized Boolean model.

13. A computer program product for generating a personalized Boolean model for a genetic disease of a patient, said computer program product comprising a computer readable storage medium having program instructions embodied therein, the program instructions being executable by a computing system to cause the computing system to:

store preliminary model data defining a preliminary model, the preliminary model corresponding to a reference model with a multiplexer at every gene node in the reference model;

generate inverse-specification data from specification data, the inverse-specification data defining an inverse-specification as the logical negation of a specification of binary measurement values;

use an interpolation-based model checker to process the inverse-specification data and the preliminary model data to generate a proof of reachability of said inverse-specification in the preliminary model with a first input of each multiplexer connected to an output thereof, said proof indicating each said multiplexer via which the inverse-specification is reachable; and generate said reference model data from the preliminary model data such that a set of gene nodes in the reference model comprises a gene node corresponding to each said multiplexer via which the inverse-specification is reachable;

store the specification data defining the specification of binary measurement values obtained from gene expression data for the patient;

store reference model data defining the reference model modeling genetic interactions for the disease, the reference model comprising a plurality of gene nodes, representing genes, connected to Boolean circuitry and a plurality of inputs for receiving binary input values representing input stimuli for the model, wherein each gene node in the set of said gene nodes comprises the multiplexer having the first input and the output which connect the gene node into the model, a second input for receiving a binary mutation value, and a control input for receiving a binary selector value controlling selective connection of one of the first and second inputs to said output, and wherein any feedback loop in the model between an output of a gene node and an input thereof contains a latch;

use a model checker to process the specification data and the reference model data to determine if said specification is reachable in the reference model via a path in which the selector value for any multiplexer in the path is selectable to permanently connect said second input to the output of that multiplexer;

if said specification is reachable, identify each multiplexer whose second input was connected to its output in the path reaching the specification to obtain mutation data for the patient, and generate a personalized Boolean model, dependent on said mutation data and the reference model, for the patient; and output personal model data defining said personalized Boolean model.

14. The computer program product of claim 13, wherein said program instructions are further executable to cause the computing system, in response to receipt of gene expression data comprising a plurality of non-binary measurement values for the patient, to generate said specification data by discretizing respective non-binary measurement values to produce said binary measurement values.

15. The computer program product of claim 13, wherein said program instructions are further executable to cause the computing system, in response to receipt of Boolean model data which defines a Boolean model modeling said genetic interactions and comprising said plurality of gene nodes, said Boolean circuitry and said plurality of inputs, to generate said reference model data from the Boolean model data such that said reference model is adapted from said Boolean model by insertion in the Boolean model of each said multiplexer and each said latch.

16. The computer program product of claim 13, wherein said program instructions are further executable to cause the computing system to specify, for each of one or more of said multiplexers, said binary mutation value for use by the model checker for that multiplexer.

17. The computer program product of claim 13, wherein said program instructions are further executable to cause the computing system to define, for each of one or more of said multiplexers, said binary mutation value for that multiplexer to be selectable by the model checker.

18. The computer program product of claim 17, wherein said program instructions are further executable such that said mutation data indicates the binary mutation value selected by the model checker for each said multiplexer whose second input was connected to its output in reaching the specification.

19. The computer program product of claim 13, wherein said program instructions are further executable to cause the computing system:

in response to receipt of gene expression data comprising a plurality of non-binary measurement values for the patient, to generate said specification data by discretizing respective non-binary measurement values to produce said binary measurement values;

in response to receipt of Boolean model data which defines a Boolean model modeling said genetic interactions and comprising said plurality of gene nodes, said Boolean circuitry and said plurality of inputs, to generate said reference model data from the Boolean model data such that said reference model is adapted from said Boolean model by insertion in the Boolean model of each said multiplexer and each said latch; and for each of one or more of said multiplexers, to define said binary mutation value for that multiplexer to be selectable by the model checker.

20. The computer program product of claim 13, wherein said program instructions are further executable to cause the computing system to define one or more of said binary input values to be selectable by the model checker.

* * * * *